US007363082B2

(12) United States Patent
Ransbury et al.

(10) Patent No.: US 7,363,082 B2
(45) Date of Patent: Apr. 22, 2008

(54) FLEXIBLE HERMETIC ENCLOSURE FOR IMPLANTABLE MEDICAL DEVICES

(75) Inventors: Terrance Ransbury, Chapel Hill, NC (US); William L. Athas, Chapel Hill, NC (US); Arthur Gwerder, Pleasanton, CA (US)

(73) Assignee: Synecor LLC, Durham, NC (US)

( * ) Notice: Subject to any disclaimer, the term of this patent is extended or adjusted under 35 U.S.C. 154(b) by 263 days.

(21) Appl. No.: 11/088,495

(22) Filed: Mar. 24, 2005

(65) Prior Publication Data

US 2006/0217779 A1   Sep. 28, 2006

(51) Int. Cl.
*A61N 1/08* (2006.01)
*A61N 1/375* (2006.01)
(52) U.S. Cl. ........................................ 607/36; 607/116
(58) Field of Classification Search ................ 607/122, 607/126
See application file for complete search history.

(56) References Cited

U.S. PATENT DOCUMENTS

| 5,613,935 A | 3/1997 | Jarvik ......................... 600/16 |
| 5,645,586 A * | 7/1997 | Meltzer .................... 623/11.11 |
| 2002/0128546 A1 | 9/2002 | Silver .......................... 600/365 |
| 2003/0060863 A1 * | 3/2003 | Dobak ......................... 607/104 |
| 2003/0158584 A1 | 8/2003 | Cates et al. .................... 607/2 |
| 2004/0172090 A1 | 9/2004 | Janzig et al. ................. 607/45 |
| 2004/0249417 A1 | 12/2004 | Ransbury et al. .............. 607/4 |
| 2004/0249431 A1 | 12/2004 | Ransbury et al. ........... 607/126 |
| 2005/0043765 A1 | 2/2005 | Williams et al. ............... 607/9 |

FOREIGN PATENT DOCUMENTS

WO    WO 2005/000398    1/2005

* cited by examiner

*Primary Examiner*—Carl Layno
*Assistant Examiner*—Tammie K. Heller
(74) *Attorney, Agent, or Firm*—Stallman & Pollock LLP

(57) ABSTRACT

A flexible, hermetically sealed enclosure device allows for the controlled insertion of an implantable device into the body of a patient. A series of bellows can be used to interconnect a number of rigid containers, each containing electronic or other components necessary for the implantable device. The bellows provide flexibility, columnar strength, and torqueability (for steering), while protecting the internal components. The bellows also can be welded to the containers to form a hermetic seal that can be electrically continous, whereby standard wiring and components can be used without fear of corrosion or contamination. Such an enclosure can be used with systems such as an intravascular implantable pacing, drug delivery, or defibrillation system.

32 Claims, 10 Drawing Sheets

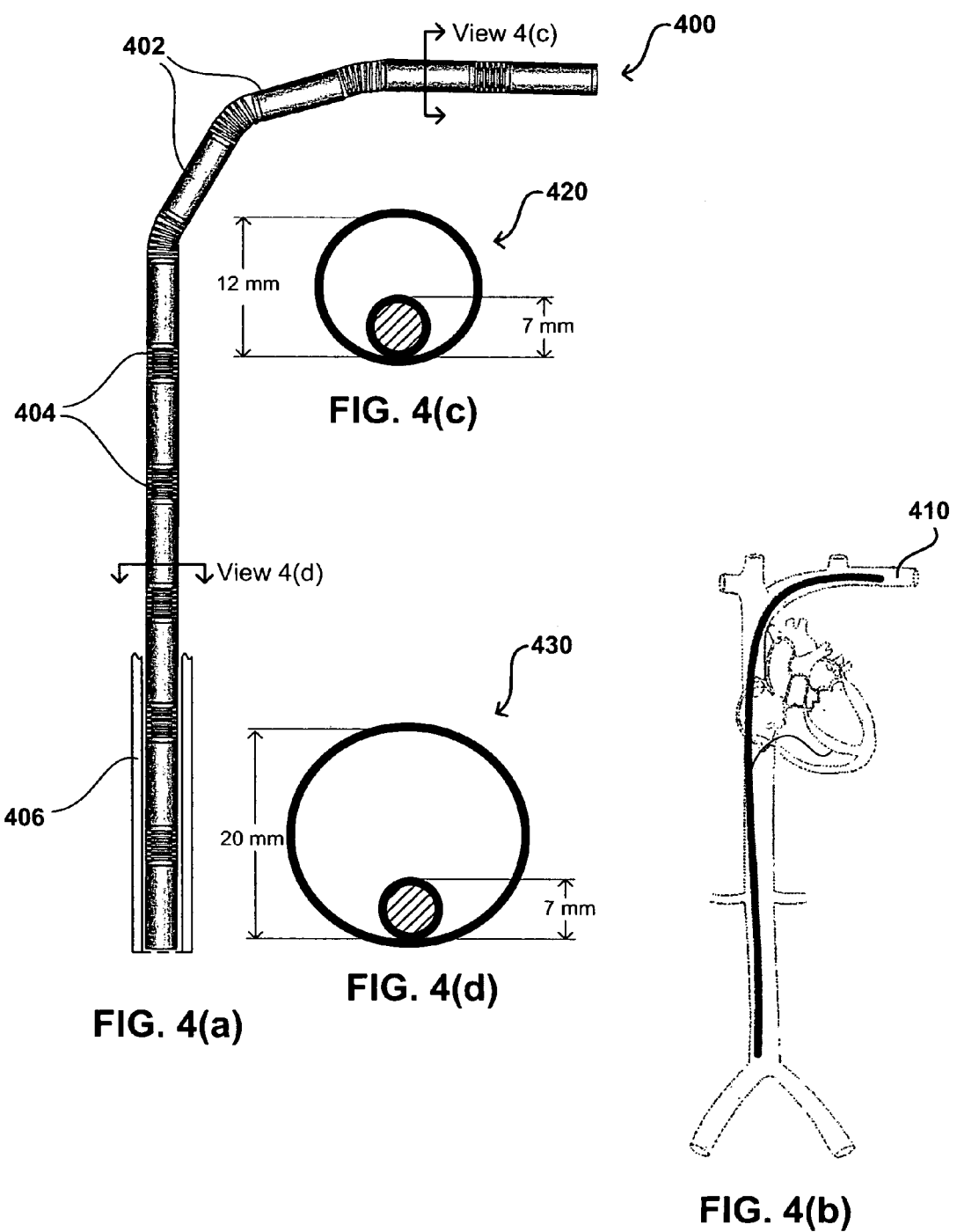

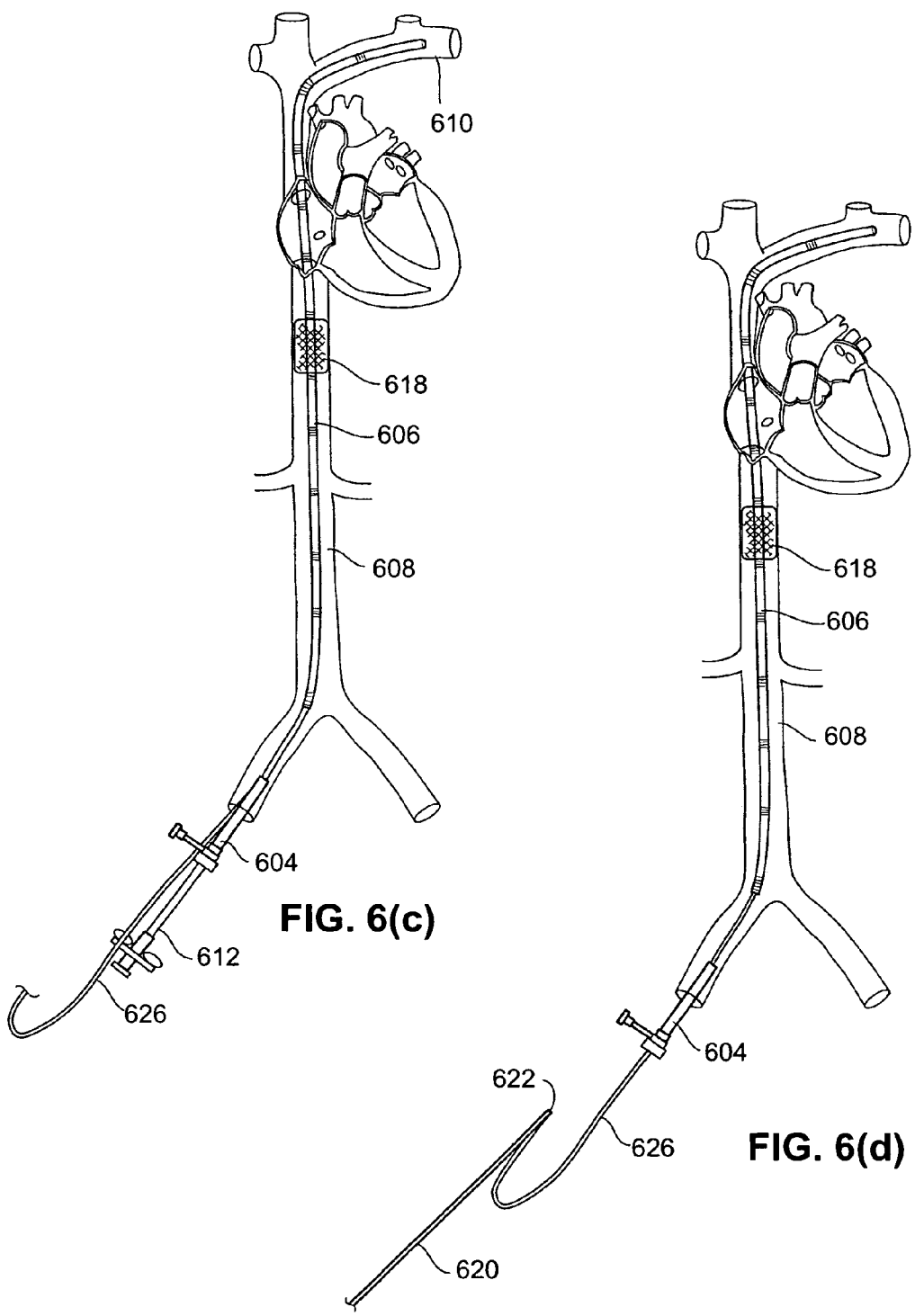

1

FLEXIBLE HERMETIC ENCLOSURE FOR IMPLANTABLE MEDICAL DEVICES

TECHNICAL FIELD OF THE INVENTION

The present invention relates to systems and methods for implanting medical devices into a patient's vasculature, such as to sense electrical activity and/or electrically stimulate the heart.

BACKGROUND

There are a number of medical devices that can have portions implanted into a patient's vasculature. For example, devices such as pacemakers, defibrillators, and implanted cardioverter defibrillators ("ICDs") have been successfully implanted for years for treatment of heart rhythm conditions. Pacemakers are implanted to detect periods of bradycardia and deliver electrical stimuli to increase the heartbeat to an appropriate rate, while ICDs are implanted in patients to cardiovert or defibrillate the heart by delivering electrical current directly to the heart. Another implantable defibrillation device can detect an atrial fibrillation (AF) episode and deliver an electrical shock to the atria to restore electrical coordination.

Next generation defibrillators, ICDs, pacemakers, etc., may take the form of elongated intravascular devices, such as those described, for example, in U.S. patent application Ser. No. 10/454,223, entitled "IMPLANTABLE INTRAVASCULAR DEVICE FOR DEFIBRILLATION AND/OR PACING," filed Jun. 4, 2003; U.S. patent application Ser. No. 10/453,971, entitled "DEVICE & METHOD FOR RETAINING A MEDICAL DEVICE WITHIN A VESSEL", filed Jun. 4, 2003; as well as U.S. patent application Ser. No. 10/862,113, entitled "INTRAVASCULAR ELECTROPHYSIOLOGICAL SYSTEM AND METHODS," filed Jun. 4, 2004, each of which is hereby incorporated herein by reference. These devices often contain electric circuitry and/or electronic components that must be hermetically sealed to prevent damage to the electronic components and the release of contaminants into the bloodstream. This can require the use of expensive shielding and insulating components, which have to be designed in a way to prevent problems with clotting and obstruction of blood flow. Further, due to the length of these implantable devices, which in some cases can be approximately 10-60 cm in length, the devices must be flexible enough to move through the vasculature while being sufficiently rigid to protect the internal components. It is desirable to simplify these devices to allow for the use of standard components that can lower the cost and complexity of these devices while still providing the necessary flexibility and support.

BRIEF DESCRIPTION OF THE DRAWINGS

FIG. 4 is (a) a perspective view illustrating the bending capability of the device of FIG. 4, as well as (b) a plan view and (c), (d) cross-sectional views of the device of FIG. 4 inserted into the vascular system of a patient.

FIGS. 6(a)-6(f) are diagrams showing a procedure for implanting a device of FIG. 5.

DETAILED DESCRIPTION

Systems and methods in accordance with embodiments of the present invention can provide for hermetic sealing of electronic and other components in the body of a patient, such as in the vasculature. Flexible methods of interconnection allow rigid containers to be moved into position inside the body while shielding the components internal to those containers from the bloodstream. The hermetic seal allows standard components to be used that are not otherwise biocompatible, allowing for simpler and cheaper devices. Because these methods of interconnection do not allow for the introduction of water vapor or other materials into the device, the implanted device will be less susceptible to corrosion and can improve the lifetime and reliability of the device.

Figures 1A, 1B:
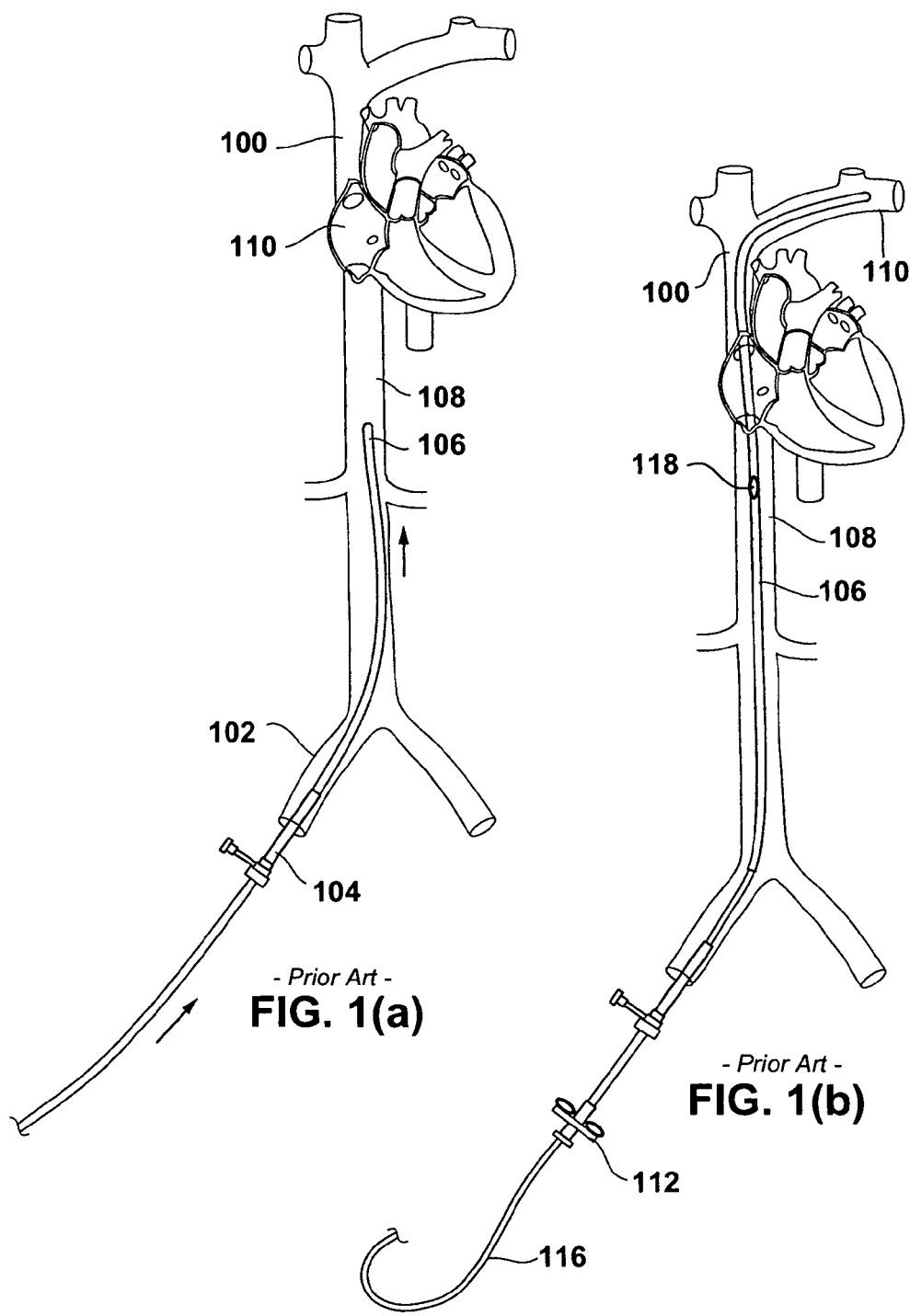
FIGS. 1(a) and (b) are schematic diagrams illustrating methods of device implantation of the prior art.

There are a number of known techniques for implanting an elongated, flexible device in the vasculature of a patient. One such technique will be described with respect to FIGS. 1(a) and 1(b). First, a small incision is formed in the femoral vein and an introducer 104 is inserted through the incision into the vein to keep the incision open during the procedure. Next, the device 106 is passed into the introducer 104, and pushed in a superior direction through the inferior vena cava ("IVC") 102, through the right atrium 110 towards the superior vena cava ("SVC") 100. With an end of the device 106 still remaining outside the body, mandrel 112 and lead 116 are attached to the exposed end of the device 106 as shown in FIG. 1(b). Pressure is applied against the mandrel 112 to advance the device 106 into the left subclavian vein ("LSV") 110. Once the device is in the target position, an anchor 118 is expanded into contact with the walls of the inferior vena cava 108. The mandrel 112 is detached from the device 106 and removed from the body.

Such a device can be implanted in a number of alternative ways, including methods described in U.S. patent application Ser. No. 10/862,113, filed Jun. 4, 2004, incorporated by reference above. For example, the device can be introduced into the venous system via the femoral vein, introduced into the venous system via that subclavian vein or the brachiocephalic veins, or into the arterial system using access through one of the femoral arteries. Moreover, different components of the intravascular systems may be introduced through different access sites. For example, a device may be separately introduced through the femoral vein and a corresponding lead may be introduced via the subclavian vein.

Figure 2:
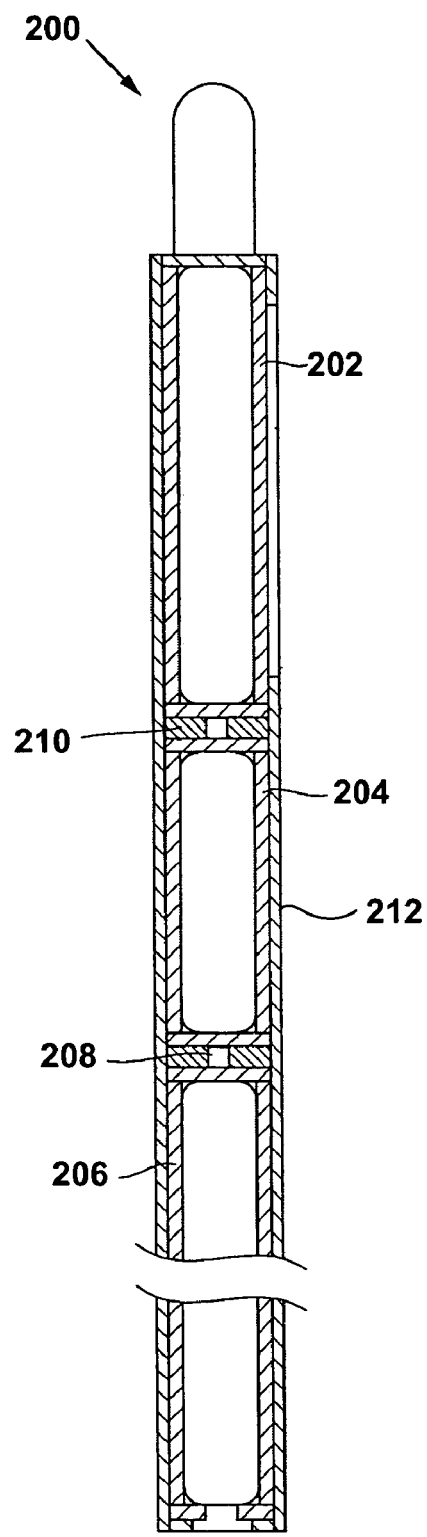
FIG. 2 is a plan view showing an intravascular electrophysiological device of the prior art.

An example of a prior device 200 that can be inserted according to the above-mentioned method is shown in FIG. 2. This device 200 includes elongate segments 202, 204, 206 defining interior space for components (not shown) to be housed within the segments. Each segment is separately enclosed by its own enclosure. The components within the enclosures are electrically connected by flex circuits 208, and the enclosures are connected using a flexible material such as silicone rubber filler to form articulations 210. The articulations 210 form hinges that bend in response to passage of the device 200 through curved regions of the vasculature. Many of these enclosures are coupled together to form the device body. A polymeric coating 112 may be formed on the exterior surface of the device.

A device in accordance with one embodiment of the present invention can provide the same functionality as the prior device of FIG. 2, while allowing use of standard components that can reduce the complexity and cost of the overall device, as well as providing other advantages. For example, FIGS. 3(*a*) and 3(*b*) show one such flexible structure 300 that can be used in accordance with various embodiments of the present invention. In this structure, one or more rigid enclosures 302, or "containers," can be used to contain electronic components to be implanted inside the vasculature of a patient. The containers can be used to house electromechanical parts or assemblies to form sophisticated implantable devices such as defibrillators, pacemakers, and drug delivery systems. These containers can be of any appropriate shape, cross-section, and length, but in this example are shown to have a cylindrical shape with a diameter of approximately 3-15 mm and a length of approximately 20 mm to 75 mm. In order to allow for insertion of the rigid components into the vasculature, it can be desirable to limit the diameter to less than about 8 mm with a length of no more than about 70 cm. Given the minimal space allowed for components, it can be desirable to arrange the device components so as to make efficient use of the available space. The length of the components can vary, depending upon the ultimate destination of each component and the path through which each component must pass, as the amount of bending and varying size of the path can affect the maximum component size for different areas of the vasculature.

The thickness of the walls of the container also can vary, depending upon the application and the material being used. It can be desirable for the walls to be as light as possible, while still providing for sufficient rigidity. In one example, the container can be made of a biocompatible material that is capable of sterilization and is conductive, with a sidewall thickness on the order of about 0.001" to 0.005". Possible materials include titanium, nitinol, stainless steel, nickel, or alloys thereof, as well as polymers such as nylon or polyurethane. The sidewall thickness can vary between containers, as well as within an individual container in order to accommodate the internal components, etc.

Depending upon the material being used, the containers can be covered by a layer or coating that may be electrically insulative, particularly if the enclosure material is conductive. One example of such a coating is ePTFE. It can be desirable to provide a coating that is anti-thrombogenic (e.g., perfluorocarbon coatings applied using supercritical carbon dioxide) so as to prevent thrombus formation on the device. It also can be beneficial for the coating to have anti-proliferative properties so as to minimize endothelialization or cellular ingrowth, since minimizing growth into or onto the device can help minimize vascular trauma when the device is explanted. The coating can also be selected to elute anti-thrombogenic compositions (e.g., heparin sulfate) and/ or compositions that inhibit cellular in-growth and/or immunosuppressive agents. If the enclosure is conductive, this layer or coating may be selectively applied or removed to leave an exposed electrode region on the surface of the enclosure where necessary.

Any appropriate number of these containers 302 can be combined using interconnecting bellows 304. Interconnecting mechanical bellows can be used to connect a number of rigid containers in order to form a flexible device. For many devices, this will include a string of at least three containers. The bellows can be of any appropriate shape, but can preferably have a shape similar in cross-section to the cross-section of the container, in order to prevent the occurrence of edges or ridges that can give rise to problems such as the formation of blood clots in the vasculature. The bellows can be made of a biocompatible material similar to the containers. Any coatings used for electrically insulating the containers and/or making the containers more hemodynamically compatible also can be used with the bellows.

The bellows can have a connector portion 306 on each end to allow the bellows to be connected with a container. A connecting process such as welding can be used to form a continuous, hermetic seal between the bellows and the containers. A sleeving 308 or overmold can be used to form an electrically continuous device, or to adjust the flexibility and/or steerability of the device. Many types of welding, using lasers or e-beams, for example, can be used to create a circular weld about the device, depending upon the necessary heating and weld thickness. The welding device can form the weld by rotating about the seam between the bellows and the containers or shell segments. The resultant weld can enclose the interior such that an elastomer is no longer needed to seal the components from the bloodstream.

By forming a hermetic seal, it is possible to use standard elements that would not otherwise be able to be implanted into the vasculature without insulating or shielding in place. For instance, as shown in the cross-section of FIG. 3(*b*), electronic or fiberoptic cabling 312, wiring, or pressure vessels can be used to transmit signals and/or power between components 310 in separate implanted containers 302, yet be isolated from the body, passing through an internal passage in the connecting bellows. Copper and other materials can be used, which are relatively inexpensive and good conductors but are not otherwise biocompatible. Without the hermetic seal, as in prior art devices, it would be necessary to run insulated wiring through a polymer such as silicone, which is not hermetic and is porous to water vapor. The water vapor passing through the silicone can leads to corrosion of the inner electrical components over time. The ability to use standard wiring and cabling allows the device to be smaller and less expensive, and less susceptible to corrosion over time.

The bellows can have a smooth inner diameter, allowing for wires and devices to be passed through without damage due to snagging. The smoothness of the inner surface also allows the bellows to be bent without pinching or applying pressure points to the inner components. The inner surface can have any appropriate shape in cross-section, but can preferably be circular or elliptical in many embodiments in order to allow for maximum flexibility in bending direction, as a rectangular bellows would be biased to four bending directions. The ratio of the length to the width of the bellows, as well as the shape of the bellows, can determine the degree of bending relative to the central axis of the bellows as would be known to one of ordinary skill in the art. While a 90° bend in one direction might be possible, with an overall bending range of 180°, it might be preferable in some embodiments to limit the bending range of the bellows to less than 45° from the central axis, in order to allow for steering of the device as well as providing some lateral strength and preventing undesired bending or angling of the containers. In other embodiments, the bending range of the bellows can be about 360°, depending on the length of the bellows, allowing for the bellows to form a U-shape. In some embodiments, it can be desirable to bias at least some of the bellows to have approximately zero bending, such that the bellows will not bend unless the path in which the bellows is placed requires such bending. In other embodiments, where the shape of the path is known for the end location of each bellows, each bellows can be biased or pre-shaped to a particular shape, curvature, or degree of bending. This not only helps to control the final shape, but can aid in the proper positioning of the device.

The sequence of devices and linking bellows can be repeated as necessary to make a device of an appropriate length. For example, FIG. 4(a) shows a device 400 having ten containers 402 connected through bellows 404, to be implanted in the vasculature as shown in FIG. 4(b). As seen in FIGS. 4(c) and 4(d), the diameter of a patient's vasculature (from about 10 mm to more than 30 mm) can be different at a first location 420 than at a second location 430. In this example, the LSV inner diameter at the first location 420 is 12 mm, while the IVC inner diameter at the second location 430 is 20 mm. Having the same outer diameter for each container, shown in this example to be about 7 mm, means that a larger percentage of the cross-sectional area of the LSV will be occupied at the first location than at the second location. In order to minimize the amount of cross-sectional area occupied by the device at each point along the LSV, the diameters of each container and/or bellows can be scaled such that the outer diameters of the containers decrease from the second location towards the first location. For example, a container at the second location might have an outer diameter of 7 mm, while a container at the first location might have an outer diameter of 5.5 mm. Further, each individual container and/or bellows can be tapered to fit the desired space in the body. For example, a container might have an outer diameter 7 mm at a first end, but taper to an outer diameter of 6.8 mm at a second end.

The device can be proportioned to be passed into the vasculature and to be anchored within the patient's vasculature with minimal obstruction to blood flow. Suitable sites for the device can include, but are not limited to, the venous system using access through the right or left femoral vein or the subclavian or brachiocephalic veins, or the arterial system using access through one of the femoral arteries. The housing of device can have a streamlined maximum cross sectional diameter which can be in the range of 3-15 mm or less, with a maximum cross-sectional diameter of 3-8 mm or less in one embodiment. The cross-sectional area of the device in the transverse direction (i.e. transecting the longitudinal axis) can preferably be as small as possible while still accommodating the required components. This area can be in the range of approximately 79 $mm^2$ or less, in the range of approximately 40 $mm^2$ or less, or between 12.5-40 $mm^2$, depending upon the embodiment and/or application.

The cross-section of the device (transecting the longitudinal axis) may have a circular cross-section, although other cross-sections including crescent, flattened, or elliptical cross-sections may also be used. It can be highly desirable to provide the device with a smooth continuous contour so as to avoid voids or recesses that could encourage thrombus formation on the device.

As discussed above, the interconnected device can be implanted using any of a number of implantation techniques. The ability of the bellows to flex, combined with the lateral strength of the interconnections, allows for some degree of steering of the device inside the body. In one embodiment, a bellows mechanism provides 1:1 torque transmission over the entire length of the overall device. This amount of torque when combined with the curvature can provide steerability when navigating the device into place within the body. In order to further help with the insertion of the device, the device can be placed inside a flexible and retractable introducer sheath 406 shown in partial cross-section in FIG. 4(a). The sheath can be made of any appropriate material, such as polyurethane or silicone, and can have any appropriate thickness and inner and outer diameters, such as an inner diameter of up to 24 French (8 mm), with wall thicknesses on the order of 0.005" and up. The sheath can be slidably positioned over the device during the insertion process, retaining any device anchor in a compressed position where applicable, then pulled from over the device after insertion. Retraction of the sheath once the device is in place allows the anchor to expand into contact with the surrounding walls of the vessel, thereby holding the medical implant in the desired location. Once deployed, the anchor can be intimate to the vessel wall, which is distended slightly, allowing the vessel lumen to remain approximately continuous despite the presence of the anchor and thus minimizing turbulence or flow obstruction. Any of a number of anchors can be used such as are known and/or used in the art. Examples of such anchors are given in U.S. patent application Ser. No. 10/862,113, incorporated herein by reference above.

In addition to the ability of the bellows to bend away from the central or long axis of the device, the bellows also allow for flexibility along the central axis of the device. The ability to flex along the central axis provides shock absorption in the long axis as well as 3-dimensional flexing. Shock absorption can help to protect the device and internal components during the implant process by minimizing the motion of the implanted device. Further, shock absorption can provide a 1:1 torque ratio for steering during the implant process. The shock absorption also can help during the life of the device, as the natural movement of the body of a patient can induce some stress on the device.

Figure 3A:
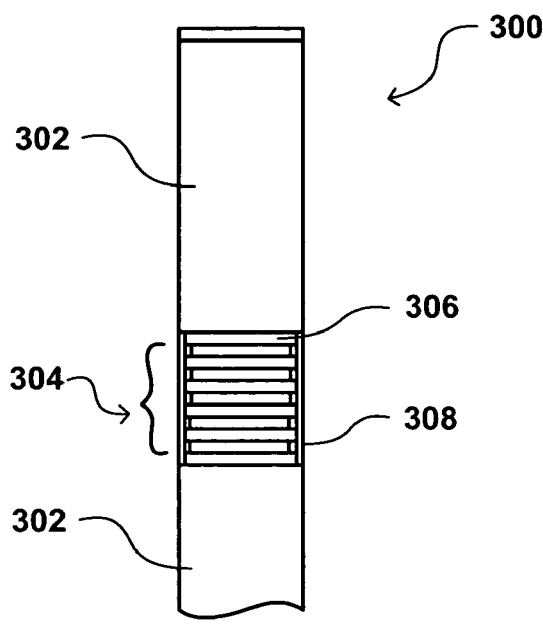
FIG. 3 is (a) a plan view and (b) a cross-section showing an intravascular electrophysiological device in accordance with one embodiment of the present invention.
Figure 3B:
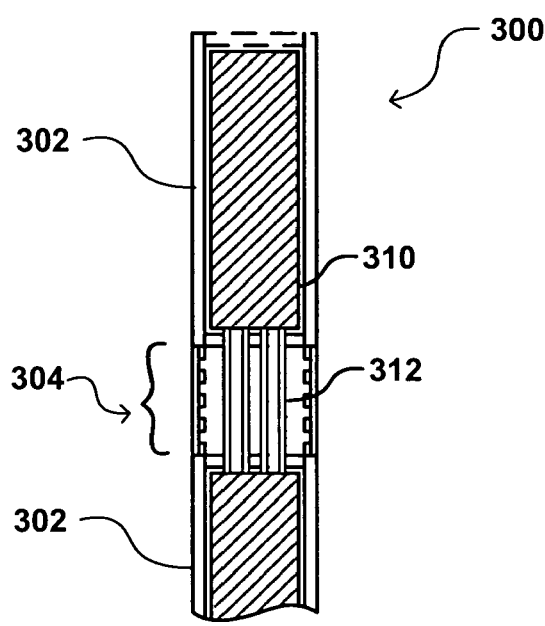

In order to further reduce stresses on the device, an overmold (such as shown in FIGS. 3 and 4) of a material such as silicone or polyurethane can be formed around the bellows to provide rigidity and columnar strength. An overmold sleeving can decrease the flexibility of the device where more rigidity is desired. An overmold sleeving also can be more flexible than the bellows such that the bellows are the primary limiting factor on flexibility. The overmold also can function to prevent the occurrence of ridges, edges, and valleys that could otherwise be present on the outside surface of the bellows. Making the outer surface of the bellows relatively smooth prevent the occurrence of turbulence and clotting of the blood that could otherwise result from a rippled bellows surface. If the device is not being implanted into the vascular system, overmolding might not be necessary.

Figure 5A:
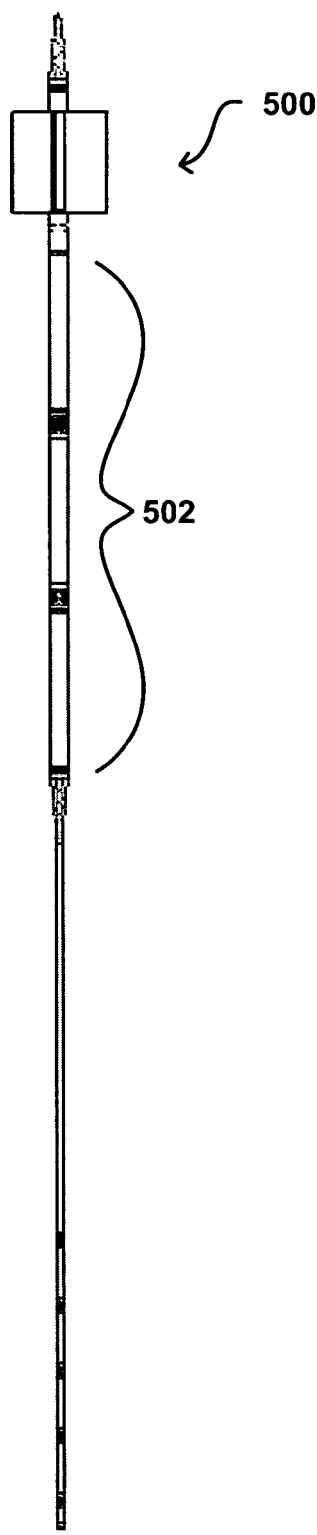
FIG. 5 includes (a)-(b) views showing a multi-chamber pacemaker and (c)-(e) views showing an implantable defibrillator including components in the interconnected, hermetically sealed casing in accordance with embodiments of the present invention.
Figure 5B:
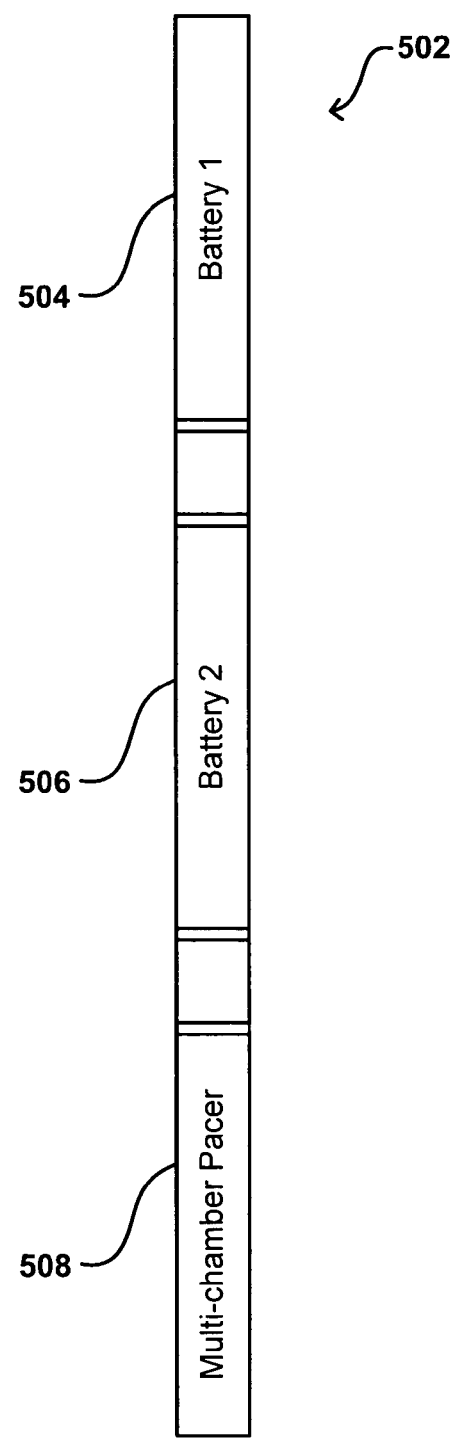
Figures 5C, 5D, 5E:
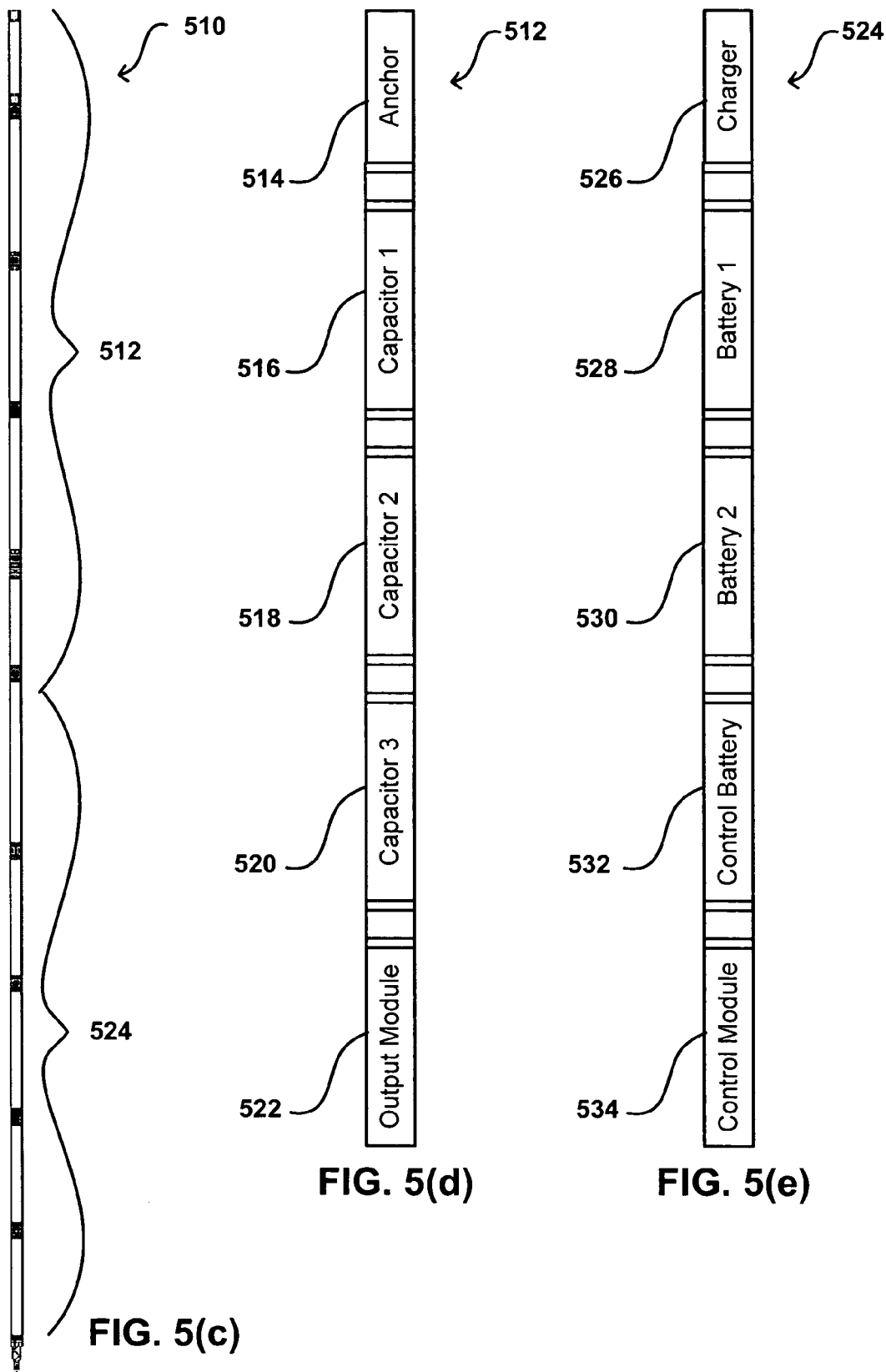
Figures 6A, 6B:
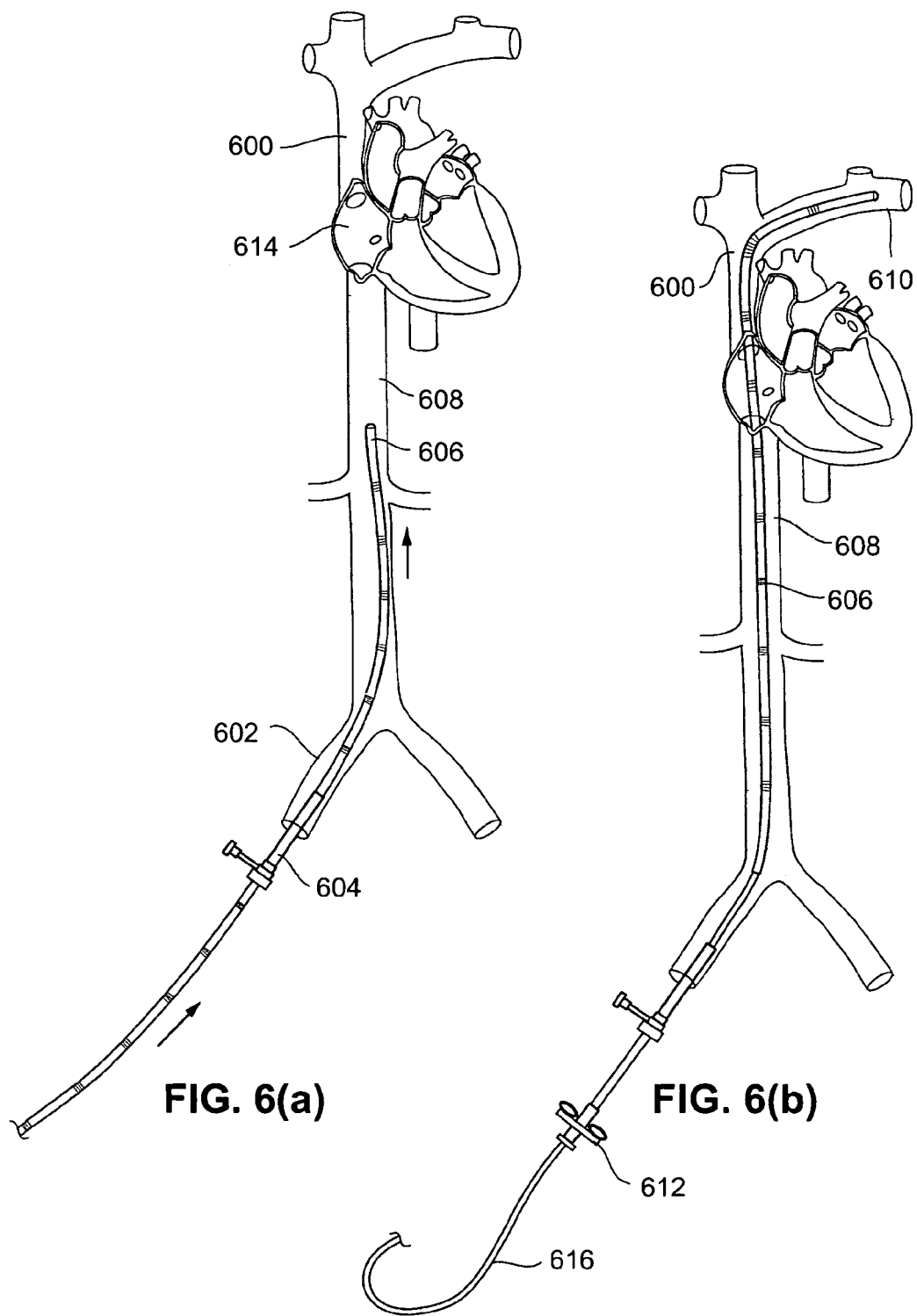
Figures 6E, 6F:
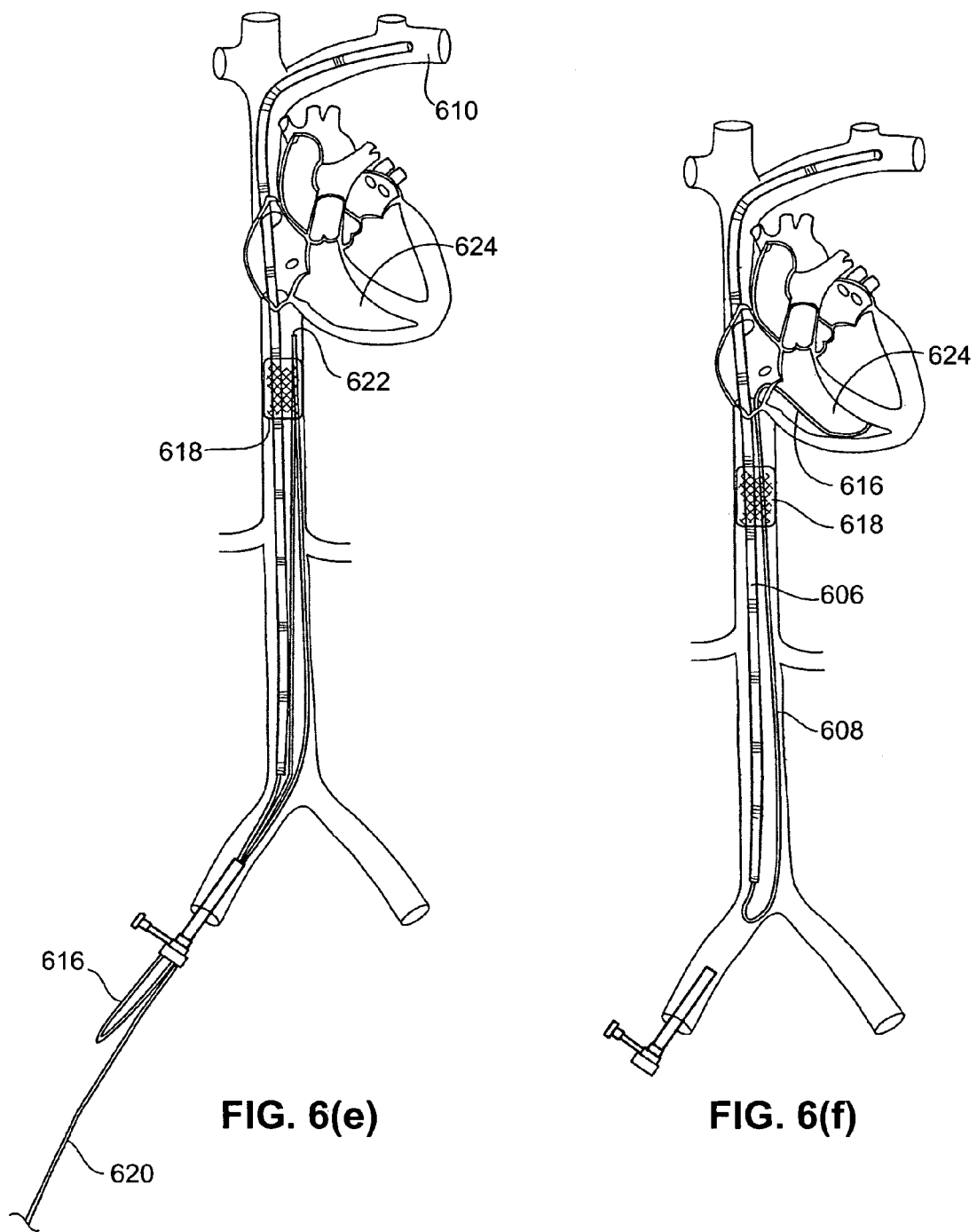

FIGS. 5(a) and (b) show a plan view and a diagram, respectively, of a multi-chamber pacemaker 500 including electronic components contained in a hermetically sealed, flexible enclosure in accordance with one embodiment of the present invention. As can be seen, the pacemaker includes in section 502 a multi-chamber pacer 508 in electrical communication with a first battery 504 and a second battery 506. Methods for making and using implantable pacemakers and the components therein are known in the art and will not be discussed in detail herein. FIGS. 5(c), (d), and (e) shown a plan view and diagrams, respectively, of an implantable defibrillator that including electronic components contained in a hermetically sealed, flexible enclosure in accordance with another embodiment of the present invention. This exemplary defibrillator includes in section 512 an anchor 514 followed by three capacitors 516, 518, 520 in electrical communication with an output module 522. In section 524, the device includes a charger 526 in electrical communication with the output module 522 and a pair of batteries 528, 530, which in turn are in electrical communication with a control battery 532 and a control module 534. Methods for making and using defibrillators and the components therein also are known in the art and will not be discussed in detail herein.

Figure 7A:
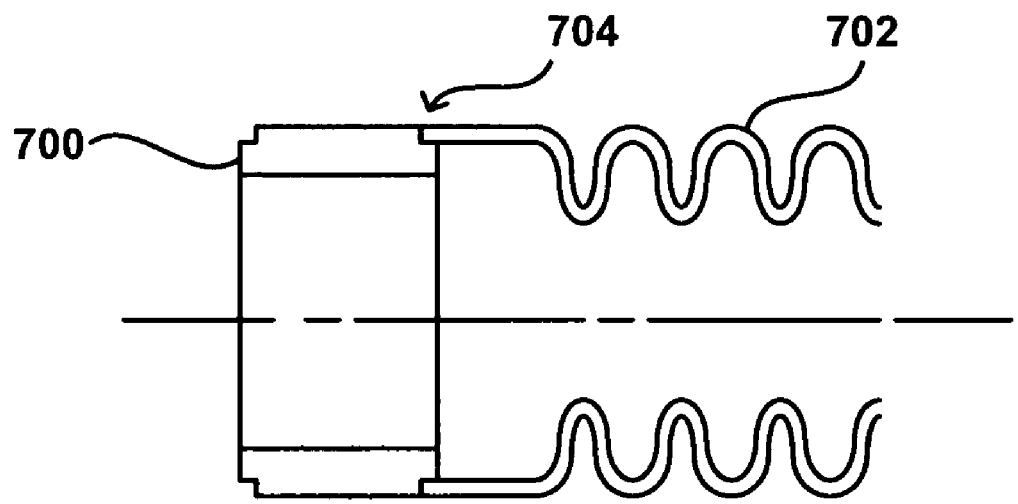
FIGS. 7(a)-7(b) show cross-sections of interconnection methods than can be used in accordance with embodiments of the present invention.
Figure 7B:
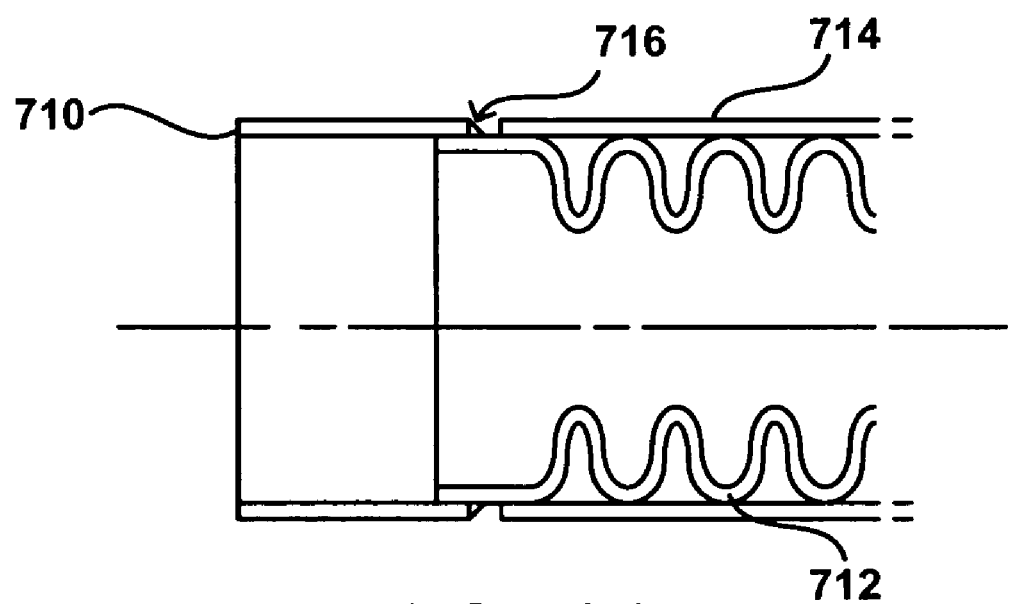

There can be a number of ways to connect the containers and bellows, such as is shown in the example of FIG. 7(a). In this example, a collar 700 is used to connect the bellows 702 to a container (not shown) opposite the bellows. The bellows can be connected to the collar 700 by any appropriate mechanism, such as a laser weld at a point of connection 704. These bellows can have a wall thickness on the order of about 0.002" in one example, formed of a material such as nickel. Another example is shown in FIG. 7(b), where a titanium cutoff ring 710 is connected to the bellows 712 via a laser weld 716. A balloon seal 714 can be placed over the bellows 712 in place of an overmold. The balloon seal 714 can be capable of expanding to fill gaps between the seal and the bellows, as well as to apply pressure to the bellows to ensure the seal remains in place during implantation. Other materials can be placed over the bellows in place of an overmold, such as a covered braid material that is capable of flexing while assisting device steerability. The volume between the covered braid and the bellows can be filed with a solid material to adjust the flexibility of the device. Other approaches are possible, such as using a molded bellows that has a sufficiently smooth exterior such that an overmold or other overlying material is not needed.

Although the embodiments are described with respect to bellows as are well known in the literature, there may be a number of other expansion joints and/or flexible and expansible vessels that can be used to connect containers in accordance with embodiments of the present invention. These devices can be made of any appropriate biocompatible material, or made of any appropriate material such as metal or polymers that are coated to be biocompatible.

Embodiments in accordance with the present invention are described primarily with respect to intravascular electrophysiological systems that may be used for a variety of functions, although any of a number of other implantable systems known and used in the art can benefit from a hermetically sealed, flexible enclosure as described herein. In general, elements of these systems include at least one device body and typically, but optionally, at least one lead coupled to the body. One or more retention devices can facilitate retention of the device body and/or leads or other elements within the vasculature. Components such as mandrels, stylets, and/or guidewires can be used to facilitate implantation of the system. Other components that can be used with such devices include those described, for example, in U.S. patent application Ser. No. 10/862,113, filed Jun. 4, 2004, which is incorporated by reference above.

Implantable devices can include components known in the art to be necessary to carry out the system functions. For example, a device can include one or more pulse generators, including associated batteries, capacitors, microprocessors, and circuitry for generating electrophysiological pulses for defibrillation, cardioversion and/or pacing. A device also can include detection circuitry for detecting arrhythmias or other abnormal activity of the heart. The specific components can depend upon the application for the device, such as whether the device is intended to perform defibrillation, cardioversion, and/or pacing along with its sensing functions.

Applications

Intravascular electrophysiological systems of the type described herein are adaptable for use in a variety of applications, including single chamber atrial or ventricular pacing, dual chamber (atrial and ventricular) pacing, bi-atrial pacing for the suppression of atrial fibrillation, bi-ventricular pacing for heart failure patients, cardioversion for ventricular tachycardia, ventricular defibrillation for ventricular fibrillation, and atrial defibrillation. The system may be adapted to perform multiple functions for use in combinations of these applications. The system may be implanted for permanent use, or it may be implanted for temporary use until more permanent interventions can be used.

In general, the system is responsive to fast and/or irregular heartbeats detected using sensing electrodes positioned on the device body and/or leads. Typically, at least two primary sensors will be positioned across the heart so as to provide a macroscopic view of the electrical activity of the heart. Common locations for these primary sensors will include a position below the heart such as the inferior vena cava, and a position above the heart such as the superior vena cava or the left subclavian vein. Data obtained from these sensors may be optionally supplemented with localized data from more closely spaced sensors at particular areas of interest, such as the right atrium. This data can bring into focus the nature of the abnormal activity detected by the primary sensors, and can allow the system to be programmed to differentiate between electrical activity requiring delivery of corrective defibrillation or pacing pulses, and electrical activity that can resolve without intervention.

The system should be programmed to deliver sufficient energy to disrupt the aberrant electrical activity and restore the heart to its normal rhythm. Energy pulses of approximately 1 J to 50 J may be used for ventricular defibrillation, whereas pulses in the range of 0.1 J to 40 J may be needed for atrial defibrillation. Pacing pulses may be delivered in the range of 0.1 to 10 Volts, with 0.1 to 2.0 millisecond pulse widths. The system may be programmed to deliver a specific amount of energy or to determine the appropriate energy level. Generally speaking, the system may be implanted to include electrodes in any vessel and/or chamber of the heart arranged to distribute energy through the heart in a manner sufficient to control the aberrant electrical activity of the heart.

An enclosure device in accordance with various embodiments of the present invention can be implanted using any of a number of implantation techniques. Many of these implantation methods are preferably carried out under fluoroscopic visualization. Although various methods described herein introduce the device into the venous system via the femoral vein, the device and components may alternatively be introduced into the venous system via that subclavian vein or the brachiocephalic veins, or into the arterial system using access through one of the femoral arteries. Moreover, different components of the intravascular systems may be introduced through different access sites. For example, a device may be separately introduced through the femoral vein and a corresponding lead may be introduced via the subclavian vein.

One such technique will be described with respect to FIGS. 6(a)-6(f) for implanting the device of FIG. 5. First, a small incision is formed in the femoral vein and an introducer 604 is inserted through the incision into the vein to keep the incision open during the procedure. Next, the device 606 is passed into the introducer 604, and pushed in a superior direction through the inferior vena cava 602

("IVC"), through the right atrium 614 towards the superior vena cava 600 ("SVC"). With an end of the device 606 still remaining outside the body, mandrel 612 and lead 616 are attached to the exposed end of the device 606 as shown in FIG. 6(*b*). Pressure is applied against the mandrel 612 to advance the device 606 into the left subclavian vein ("LSV") 610.

Referring to FIG. 6(*c*), once the device 606 is in the target position, the anchor 618 is expanded into contact with the walls of the inferior vena cava 608. The anchor can self-expand and/or be expanded using an inflation tool, such as a balloon passed into the anchor's central lumen and subsequently inflated. When the anchor is expanded, the radial force engages the device 606 and secures the device 606 against the vessel wall. The mandrel 612 then can be detached from the device 606 and removed from the body.

A steerable guidewire or stylet 620 can be attached to the free end 622 of the lead 626 or inserted into a lumen in the lead 626, which can be used to carry the free end 622 of the lead through the introducer 604 and into the IVC 602, such that the lead 616 folds over on itself as shown in FIG. 6(*e*). The free end 622 is steered into the right ventricle 624 ("RV") using the stylet 620, and is fixed in place using a helical screw member at the free end 622 or another attachment feature. The stylet 620 then can be removed, leaving the lead 626 positioned in the right ventricle 624 as shown in FIG. 6(*f*). As an alternative, the free end 622 of lead 626 can be steered into the middle cardiac vein.

It should be pointed out that many of the device configurations, components, retention devices and methods, implantation methods and other features are equally suitable for use with other forms of intravascular implants. Such implants might include, for example, implantable neurostimulators, artificial pancreas implants, diagnostic implants with sensors that gather data such as properties of the patient's blood (e.g. blood glucose level) and/or devices that deliver drugs or other therapies into the blood from within a blood vessel. More particularly, fully implantable intravascular systems may be used for administering drugs including hormones, chemotherapeutic agents, pharmaceuticals, synthetic, recombinant or natural biologics, and other agents within the body. Generally speaking, the systems include drug reservoirs and associated components (e.g. batteries, electronics, motors, pumps, circuitry, telemetric components, sensors) that are anchored in the vasculature and programmed to administer drugs into the bloodstream or directly into certain organs or tissues. Drug delivery microtubules may extend from the device body and into surrounding vessels in a similar way that the leads in the embodiments described above extend from the device body. These microtubules may be positioned within the vasculature to deliver drugs directly into the bloodstream, and/or they may extend from the device through the vascular into or near a body organ. For example, by directing drugs to a particular aortic branch (e.g. hepatic artery, renal artery, etc), an intravascular delivery device can achieve target delivery of therapeutic drugs to specific organs including the brain, liver, kidneys etc.

In some embodiments, such intravascular drug delivery systems may be controlled remotely using telemetry or via internal intelligence that may be responsive to in-situ sensing of biological, physical or biochemical parameters.

It also should be pointed out that, although the embodiments have been described in the context of intravascular implants, alternative embodiments may be used to house medical devices implanted elsewhere in the body, including subcutaneous pockets, body organs, or other body cavities.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. A flexible enclosure for implantation in a body, comprising:
   a plurality of rigid containers, each container operable to contain at least one electronic component wholly within that container, the plurality of rigid containers configured to be implanted into the body as part of a chronically implanted device wholly implanted within the body; and
   a plurality of mechanical bellows, each bellows connecting two of the rigid containers to form an elongated chain of containers and bellows, each bellows further having an internal passage allowing for interconnection of the components in the rigid containers wherein the flexible enclosure is operable to be implanted in the vasculature of the body.

2. A flexible enclosure according to claim 1, wherein:
   each connection between a bellows and a container forms a hermetic seal.

3. A flexible enclosure according to claim 1, wherein:
   each bellows allows for flexing over a range of about 360 degree.

4. A flexible enclosure according to claim 1, wherein:
   each of the containers is formed of a biocompatible material.

5. A flexible enclosure according to claim 1, wherein:
   each of the containers is formed of a material selected from the group consisting of titanium, nitinol, stainless steel, nickel, and biocompatible polymers.

6. A flexible enclosure according to claim 1, wherein:
   each of the bellows is formed of a biocompatible material.

7. A flexible enclosure according to claim 1, wherein:
   each of the bellows is formed of a material selected from the group consisting of titanium, nitinol, stainless steel, nickel, and biocompatible polymers.

8. A flexible enclosure according to claim 1, wherein:
   each of the containers is cylindrical in shape.

9. A flexible enclosure according to claim 1, wherein:
   each of the containers and bellows has a diameter in the range of about 3 mm to about 15 mm.

10. A flexible enclosure according to claim 1, wherein:
    each of the containers and bellows has a diameter in the range of about 3 mm to about 8 mm.

11. A flexible enclosure according to claim 1, wherein:
    each of the containers and bellows is covered by an electrically insulative coating.

12. A flexible enclosure according to claim 1, wherein:
    at least one of the bellows is pre-shaped to have a particular curvature.

13. A flexible enclosure according to claim 1, further comprising:
    a retractable introducer sheath shaped to fit around the connected containers and bellows.

14. A flexible enclosure according to claim 13, further comprising:
an anchor connected to one of the containers and operable to be compressed when covered by the sheath, the anchor further operable to expand upon retraction of the sheath in order to hold the position of the enclosure in the body.

15. A flexible enclosure according to claim 1, wherein: each bellows provides for three-dimensional flexing.

16. A flexible enclosure according to claim 1, wherein: each bellows provides shock absorption.

17. A flexible enclosure according to claim 1, further comprising:
a sleeving over each bellows.

18. A flexible enclosure according to claim 17, wherein: the sleeving is formed of one of silicone and polyurethane.

19. A flexible enclosure according to claim 1, wherein: the connected plurality of rigid containers and plurality of mechanical bellows provides 1:1 torque transmission over an entire length of the flexible enclosure.

20. A flexible enclosure according to claim 19, wherein: the torque transmission provides steerability when navigating the flexible enclosure into place within the body.

21. A flexible enclosure for implantation in a body, comprising:
a plurality of cylindrical containers, each container operable to contain at least one electronic component wholly within that container, the plurality of cylindrical containers configured to be implanted into the body as part of a chronically implanted device wholly implanted within the body; and
a plurality of cylindrical bellows, each bellows connecting two of the rigid containers to form an elongated array of containers and bellows, each bellows being welded to the corresponding two containers to form a hermetic seal such that an internal passage in the bellows allows for interconnection of the components using non-biocompatible materials wherein the flexible enclosure is operable to be implanted in the vasculature of the body.

22. A flexible enclosure according to claim 21, wherein: the plurality of cylindrical bellows and rigid containers form an electrically continuous structure.

23. A flexible enclosure according to claim 21, wherein: the plurality of cylindrical bellows and rigid containers form a continuous structure that shields components inside the continuous structure.

24. A flexible enclosure according to claim 21, wherein: each of the containers and bellows is formed of a biocompatible material.

25. A flexible enclosure according to claim 21, wherein: each of the containers is formed of a material selected from the group consisting of titanium, nitinol, stainless steel, nickel, gold plating, propylene, and biocompatible polymers.

26. A flexible enclosure according to claim 21, wherein: each of the bellows is formed of a material selected from the group consisting of titanium, nitinol, stainless steel, nickel, and biocompatible polymers.

27. A flexible enclosure according to claim 21, wherein: each of the containers and bellows has a diameter in the range of about 3 mm to about 15 mm.

28. A flexible enclosure according to claim 21, wherein: each of the containers and bellows has a diameter in the range of about 3 mm to about 8 mm.

29. A flexible enclosure according to claim 21, wherein: each of the containers and bellows is covered by an electrically insulative coating.

30. A flexible enclosure according to claim 21, wherein: at least one of the bellows is pre-shaped to have a particular curvature.

31. A flexible enclosure according to claim 21, further comprising:
a retractable introducer sheath shaped to fit around the connected containers and bellows.

32. A flexible enclosure according to claim 31, further comprising:
an anchor connected to one of the containers and operable to be compressed when covered by the sheath, the anchor further operable to expand upon retraction of the sheath in order to hold the position of the enclosure in the body.

* * * * *